(12) United States Patent
Kato et al.

(10) Patent No.: US 9,753,005 B2
(45) Date of Patent: Sep. 5, 2017

(54) SOX CONCENTRATION DETECTION DEVICE

(71) Applicant: TOYOTA JIDOSHA KABUSHIKI KAISHA, Toyota-shi, Aichi-ken (JP)

(72) Inventors: Tetsuya Kato, Okazaki (JP); Shinya Teranishi, Aichi-ken (JP); Keiichiro Aoki, Shizuoka-ken (JP); Kazuhiro Wakao, Susono (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 22 days.

(21) Appl. No.: 14/760,528

(22) PCT Filed: Dec. 26, 2013

(86) PCT No.: PCT/JP2013/084844
§ 371 (c)(1),
(2) Date: Jul. 13, 2015

(87) PCT Pub. No.: WO2014/112315
PCT Pub. Date: Jul. 24, 2014

(65) Prior Publication Data
US 2015/0355136 A1 Dec. 10, 2015

(30) Foreign Application Priority Data
Jan. 15, 2013 (JP) ................. 2013-004509

(51) Int. Cl.
*G01N 27/407* (2006.01)
*G01N 33/00* (2006.01)

(52) U.S. Cl.
CPC ..... *G01N 27/4074* (2013.01); *G01N 33/0042* (2013.01)

(58) Field of Classification Search
CPC ......... G01N 27/403–27/4078; G01N 33/0042; G01N 27/406–27/41
See application file for complete search history.

(56) References Cited

U.S. PATENT DOCUMENTS

| | | | |
|---|---|---|---|
| 6,084,418 A | 7/2000 | Takami et al. | |
| 6,439,038 B1* | 8/2002 | Rosel | F01N 11/007 73/114.32 |
| 2008/0140301 A1* | 6/2008 | Ding | G01N 27/407 701/115 |

FOREIGN PATENT DOCUMENTS

| JP | H10-73561 A | 3/1998 |
|---|---|---|
| JP | 2009-244279 A | 10/2009 |

* cited by examiner

Primary Examiner — J. Christopher Ball
(74) Attorney, Agent, or Firm — Andrews Kurth Kenyon LLP (57) ABSTRACT

To provide an SOx concentration detection device that can detect the SOx concentration in exhaust gas without using a dedicated sensor. As shown in FIG. 4, the current value that flows when a voltage in the limiting current region is applied stays at a constant value (limiting current value) regardless of the elapsed time. On the other hand, the current value that flows when a voltage in the overcurrent region is applied decreases with the lapse of time and approaches the limiting current value 30 seconds after the start of application of the voltage. In this embodiment, the current value difference is defined as "$SO_2$ reduction current," and the $SO_2$ concentration around the sensor is detected from an integrated value of the $SO_2$ reduction current.

3 Claims, 4 Drawing Sheets

SOX CONCENTRATION DETECTION DEVICE

CROSS-REFERENCE TO RELATED APPLICATIONS

This is a national phase application based on the PCT International Patent Application No. PCT/JP2013/084844 filed Dec. 26, 2013, claiming priority to Japanese Patent Application No. 2013-004509 filed Jan. 15, 2013, the entire contents of both of which are incorporated herein by reference.

TECHNICAL FIELD

The present invention relates to an SOx concentration detection device, and, more particularly, to an SOx concentration detection device capable of detecting the concentration of SOx in exhaust gas from an internal combustion engine.

BACKGROUND ART

A device that detects the SOx concentration in exhaust gas from an internal combustion engine using a gas sensor that includes a catalyst that captures S components in the exhaust gas when the exhaust gas air-fuel ratio is lean and releases the captured S components when the exhaust gas air-fuel ratio is stoichiometric or rich, and a temperature measurement device that measures the temperature of the catalyst has already been disclosed in Patent Literature 1, for example.

A limiting current-type sensor is disclosed in Patent Literature 2 and 3. The sensor includes a solid electrolyte that has oxide ion conductivity and a pair of electrodes that are provided on opposite sides of the solid electrolyte, and detects the $O_2$ concentration in exhaust gas based on a limiting current that is generated when a predetermined voltage is applied between the pair of electrodes. In addition, it is disclosed in Patent Literature 2 that the sensor is deteriorated when S components in the exhaust gas are adsorbed on the sensor electrodes.

RELATED ART LITERATURE

Patent Literature

Patent Literature 1: Japanese Patent Application Publication No. 2009-244279 (JP 2009-244279 A)
Patent Literature 2: Japanese Patent Application Publication No. 10-073561 (JP 10-073561 A)
Patent Literature 3: Japanese Patent Application Publication No. 11-132996 (JP 11-132996 A)

SUMMARY OF THE INVENTION

Problem to be Solved by the Invention

The gas sensor of Patent Literature 1 focuses on the S adsorption characteristics of the catalyst, and the catalyst that has such S adsorption characteristics is essential for the SOx concentration detection in Patent Literature 1. It can be, therefore, mentioned that the gas sensor is a dedicated sensor for SOx concentration detection. A dedicated sensor must be installed in addition to existing sensors. Thus, the problems of installation space and cost increase are unavoidable.

In this regard, the limiting current-type sensor of Patent Literature 2 or 3 is a sensor that is generally installed in an exhaust passage of an internal combustion engine for the purpose of measuring the $O_2$ concentration in exhaust gas and therefore does not cause the above-mentioned problems. However, a device that uses a limiting current-type sensor to detect the SOx concentration in exhaust gas from an internal combustion engine is not found in related art literature including the above-mentioned Patent Literature.

The present invention has been made in view of the above-mentioned problems. In other words, it is an object of the present invention to provide a novel SOx concentration detection device that uses a limiting current-type sensor.

Means for Solving the Problem

A first invention provides an SOx concentration detection device that includes: a limiting current-type sensor that includes a solid electrolyte that has oxide ion conductivity and a pair of electrodes that are provided on opposite sides of the solid electrolyte, and generates a limiting current corresponding to the concentration of a specific component in the exhaust gas from an internal combustion engine when a predetermined voltage is applied between the pair of electrodes; and SOx concentration detection means that applies a reference voltage in a limiting current region that includes the predetermined voltage and an SOx detecting voltage in a voltage region higher than the limiting current region between the pair of electrodes when the exhaust gas air-fuel ratio of the internal combustion engine is on the rich side of stoichiometry to acquire an SOx detecting output that is output from the sensor when the SOx detecting voltage is applied and a reference output that is output from the sensor when the reference voltage is applied, and detects the SOx concentration in the exhaust gas from the internal combustion engine using histories of the SOx detecting output and the reference output that are generated before the output difference between the SOx detecting output and the reference output falls to or below a set value.

A second invention provides the SOx concentration detection device according to the first invention, in which the pair of electrodes include a detection electrode that is provided on an exhaust gas contacting surface of the solid electrolyte, and the detection electrode contains 0.1 to 5.0 wt % of at least one metal that is selected from the group that consists of alkaline-earth metals and rare-earth metals.

A third invention provides the SOx concentration detection device according to the first or second invention, in which the SOx concentration detection means controls the exhaust gas air-fuel ratio to the richer side of stoichiometry and heats the sensor to a predetermined temperature at which the S components that have been adsorbed on the pair of electrodes can be desorbed when the output difference falls to or below the set value.

Effect of the Invention

The present inventors found a correlation between the histories of sensor outputs (the SOx detecting output and the reference output) that are outputs when a reference voltage in the limiting current region and the SOx detecting voltage are applied between the pair of electrodes when the exhaust gas air-fuel ratio of an internal combustion engine is on the rich side of stoichiometry and the amount of SOx that has been adsorbed on the surfaces of the pair of electrodes. The first invention is based on this finding. In other words, according to the first invention, a novel device capable of detecting the SOx concentration in exhaust gas using a limiting current-type sensor can be provided.

The present inventors also found that both promotion of SOx adsorption on the detection electrode and easy restoration from sensor poisoning by adsorbed SOx can be achieved when the detection electrode of the sensor contains 0.1 to 5.0 wt % of at least one metal that is selected from the group that consists of alkaline-earth metals and rare-earth metals. The second invention is based on this finding. According to the second invention, a sensor suitable for the detection of SOx concentration by the first invention can be provided.

In the first invention, when the SOx detecting voltage is applied between the pair of electrodes, the SOx that has been adsorbed on the surfaces of the pair of electrodes is reduced to S and the S remains adsorbed on the pair of electrodes. In this regard, according to the third invention, when the output difference falls to or below the set value, the exhaust gas air-fuel ratio is controlled to the rich side of stoichiometry and the sensor is heated to a predetermined temperature at which the S components that have been adsorbed on the pair of electrodes can be desorbed. Thus, it is possible to start desorption of the S on the pair of electrodes immediately after the completion of acquisition of the histories of sensor outputs that are necessary for the detection of SOx concentration. In other words, the S on the pair of electrodes can be desorbed at the best time to improve the accuracy of the next and subsequent detections of the SOx concentration.

MODES FOR CARRYING OUT THE INVENTION

[Description of Device Configuration]

Figure 1:
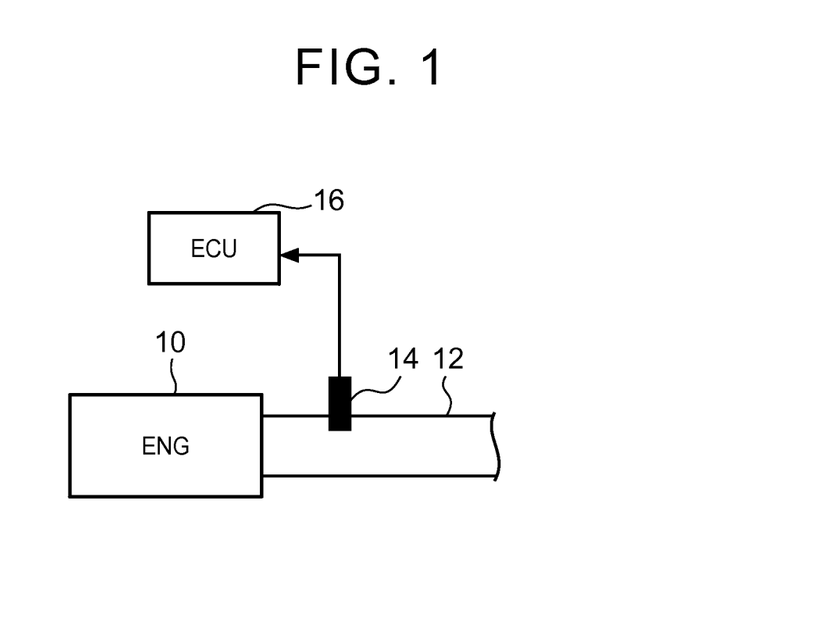
FIG. 1 is a diagram that illustrates the configuration of an SOx concentration detection device according to this embodiment.

An embodiment of the present invention is hereinafter described with reference to FIG. 1 to FIG. 9. FIG. 1 is a diagram that illustrates the configuration of an SOx concentration detection device according to this embodiment. As shown in FIG. 1, the SOx concentration detection device according to this embodiment includes an engine 10 as a power source for a vehicle. The number and arrangement of cylinders of the engine 10 are not specifically limited. An A/F sensor 14 is installed in an exhaust passage 12 of the engine 10. The A/F sensor 14 is a limiting current-type sensor that outputs a current signal in proportion to the oxygen concentration in exhaust gas or the like in response to application of a voltage (its details are described later).

The SOx concentration detection device of this embodiment includes an ECU (Electronic Control Unit) 16. Various sensors necessary for control of the A/F sensor 14 and the engine 10 (such as a crank angle sensor that detects the engine speed and an air flow meter that detects the intake air amount) are electrically connected to the input side of the ECU 16. Various actuators, such as injectors (not shown) that inject fuel into the respective cylinders of the engine 10, are electrically connected to the output side of the ECU 16. The ECU 16 executes predetermined programs based on input information from the various sensors and drives the various actuators and so on to perform various control functions regarding the operation of the engine 10.

[A/F Sensor 14]

Figure 2:
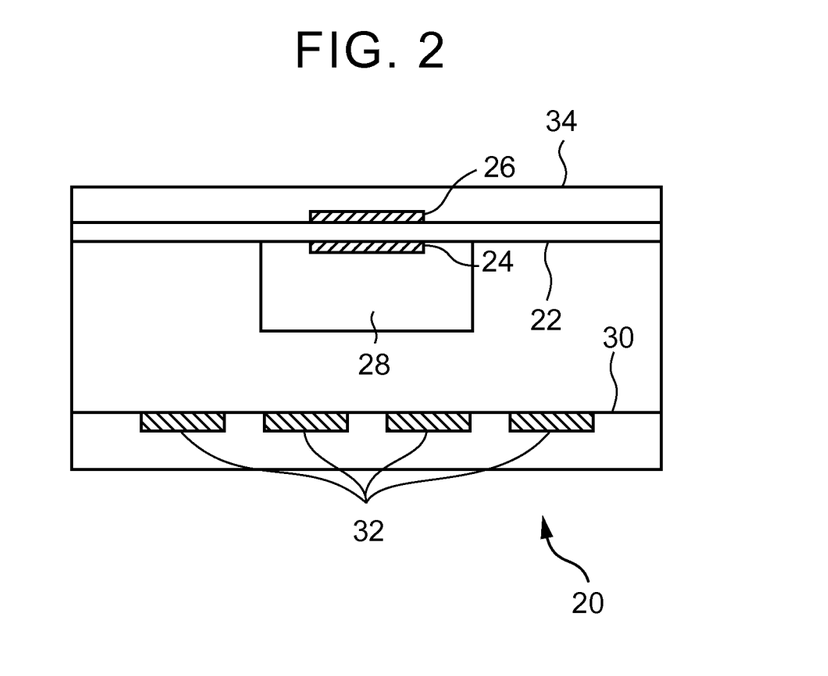
FIG. 2 is a cross-sectional schematic view of a sensor element of an A/F sensor 14 of FIG. 1.

FIG. 2 is a cross-sectional schematic view of a sensor element of an A/F sensor 14 of FIG. 1. As shown in FIG. 2, a sensor element 20 includes a solid electrolyte 22 composed of stabilized zirconia. The stabilized zirconia is a zirconium-based solid electrolyte ($ZrO_2$-$M_2O_3$ solid solution or $ZrO_2$-MO solid solution (M: Y, Yb, Gd, Ca or Mg)), for example, and exhibits oxygen ion conductivity at high temperatures.

The sensor element 20 also includes electrodes 24 and 26 that are formed on opposite sides of the solid electrolyte 22. The electrodes 24 and 26 are primarily composed of Pt and electrically connected to each other by a lead (not shown). Preferred accessory components in the electrode 26 and their amounts of addition are described later. The electrode 24 is located on the same side as an air duct 28 for atmosphere introduction, and opposed to a heater base material 30. The heater base material 30 is composed of a ceramic (such as alumina), and has built-in heating elements 32 that generate heat when supplied with electricity from an in-vehicle battery power source (not shown). A diffusion layer 34 is placed over the electrode 26 to cover it. The diffusion layer 34 is composed of a heat-resistant porous ceramic (such as porous alumina), for example.

The exhaust gas that flows through the exhaust passage 12 flows through the diffusion layer 34 and comes into contact with the electrode 26. At this time, when a voltage is applied between the electrodes 24 and 26, a current flows differently depending on the exhaust gas air-fuel ratio. Specifically, when the exhaust gas air-fuel ratio is in the lean side region (A/F>14.7), the excess $O_2$ in the exhaust gas reacts on the electrode 26, and receives electrons and gets ionized. The resulting oxygen ions ($O^{2-}$) migrate through the solid electrolyte 22 and reach the electrode 24. This migration of $O^{2-}$ results in a current flow from the electrode 24 to the electrode 26. The $O^{2-}$ that has reached the electrode 24 releases electrons and returns to $O_2$, and then is discharged into the air duct 28. On the other hand, when the exhaust gas air-fuel ratio is in the rich side region (A/F<14.7), the $O_2$ in the air duct 28 reacts on the electrode 24, and receives electrons and turns into $O^{2-}$. The $O^{2-}$ migrates through the solid electrolyte 22. When the $O^{2-}$ reaches the electrode 26, it reacts with unburned components (such as HC, CO and $H_2$) in the exhaust gas and turns into $CO_2$ and $H_2O$. This migration of $O^{2-}$ results in a current flow from the electrode 26 to the electrode 24.

[Method for Detecting Exhaust Gas Air-Fuel Ratio Using A/F Sensor 14]

Figure 3:
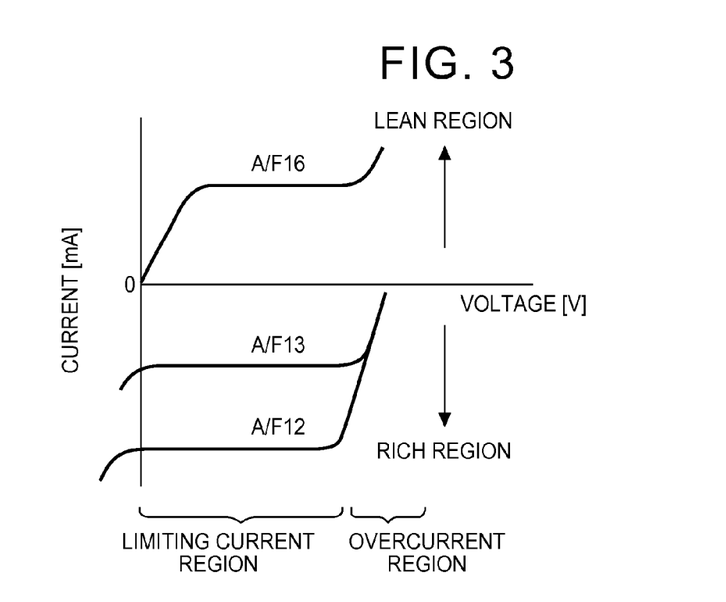
FIG. 3 is a current-voltage characteristic diagram of the A/F sensor 14.

A method for detecting the exhaust gas air-fuel ratio using the A/F sensor 14 is next described briefly with reference to FIG. 3. FIG. 3 is a current-voltage characteristic diagram of the A/F sensor 14. As shown in FIG. 3, there is a region in which the current hardly changes but remains constant even when the voltage that is applied between the electrodes 24 and 26 is varied. This current value is called "limiting current value," and the voltage region corresponding to this limiting current value is called "limiting current region." In addition, as shown in FIG. 3, the limiting current value increases as the exhaust gas air-fuel ratio is shifted to the leaner side and decreases as the exhaust gas air-fuel ratio is shifted to the richer side. The detection of the exhaust gas air-fuel ratio using the A/F sensor 14 is achieved based on this correlation. Specifically, a predetermined voltage in the limiting current region (such as 0.3 V) is applied between the electrodes 24 and 26, and a current signal that is output from the A/F sensor 14 at this time is acquired. Then, the exhaust gas air-fuel ratio is detected by comparing the current signal with the limiting current value.

[Characteristics of this Embodiment]

As shown in FIG. 3, there is a region in which the current value increases on the high voltage side of the limiting current region. This region is called "overcurrent region," and it is considered that the electron conduction that is induced by reduction of the electrolyte that has been adsorbed on the sensor element 20 (specifically, on the surfaces of the electrode 26) contributes to the increase of the current value. The present inventors conducted studies focusing on the phenomenon in which the current value increases, and, consequently, found a correlation between the amount of $SO_2$ that has been adsorbed on the surfaces of the electrode 26 (which is hereinafter also referred to as "electrode surface $SO_2$ adsorption amount") and the change in the current value with the lapse of time. This finding is described with reference to FIG. 4 to FIG. 6.

Figure 4:
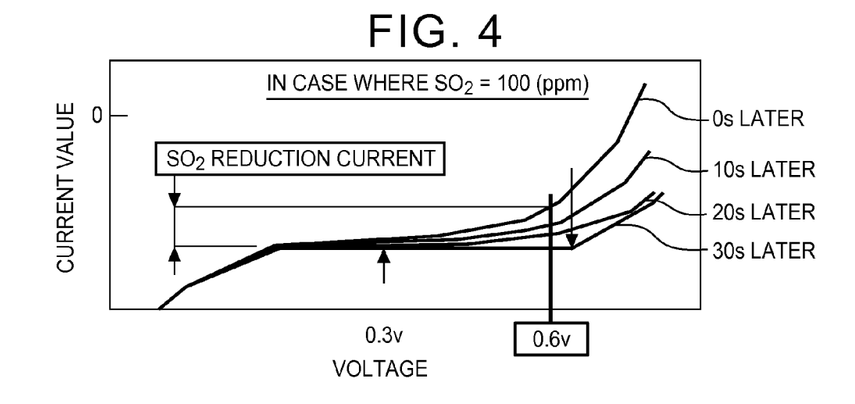
FIG. 4 is a current-voltage characteristic diagram of the A/F sensor 14 that is obtained under measurement conditions including an $SO_2$ concentration around the sensor of 100 ppm and a rich air-fuel ratio (fixed value).

FIG. 4 is a current-voltage characteristic diagram of the A/F sensor 14 that is obtained under measurement conditions including an $SO_2$ concentration around the sensor of 100 ppm and a rich air-fuel ratio (fixed value). The characteristic curves that are shown in FIG. 4 correspond to respective elapsed times (0 second later, 10 seconds later, 20 seconds later and 30 seconds later) after the start of application of a voltage. As shown in FIG. 4, the current value that flows when a voltage in the limiting current region (0.3 V) is applied stays at a constant value (limiting current value) regardless of the elapsed time. On the other hand, the current value that flows when a voltage in the overcurrent region (0.6 v) is applied decreases with the lapse of time and approaches the limiting current value 30 seconds after the start of application of the voltage.

As described above, the electron conduction that is induced by reduction of the electrolyte that has been adsorbed on the surfaces of the electrode 26 contributes to the phenomenon in which the current value increases in the overcurrent region. It is, therefore, natural to believe that this electron conduction also contributes to the phenomenon in which the current decreases as observed in FIG. 4. It has been known, however, that the $SO_2$ that has been adsorbed on the surfaces of the electrode 26 does not react easily except on special occasions such as the case where S poisoning recovery control as described later is performed. Thus, in order to discover the relationship between the phenomenon in which the current decreases as observed in FIG. 4 and $SO_2$ that has been adsorbed on the surfaces of the electrode 26, the present inventors investigated the current-voltage characteristics of the A/F sensor 14 by varying the $SO_2$ concentration of the measurement conditions in FIG. 4.

Figure 5:
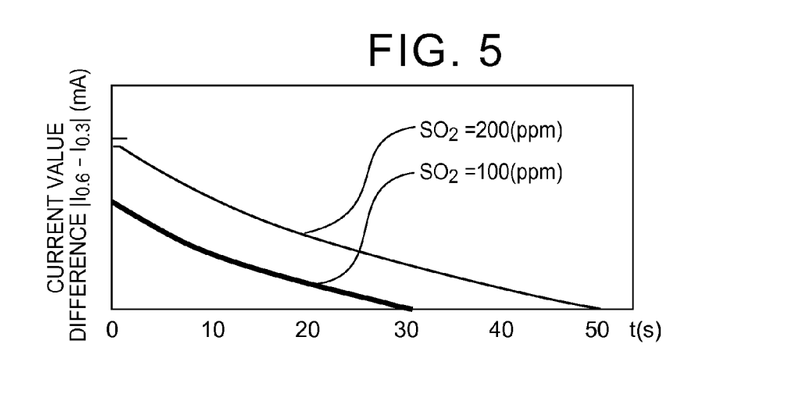
FIG. 5 is a diagram that shows the results of an investigation of the current-voltage characteristics of the A/F sensor 14 that was conducted by varying the $SO_2$ concentration of the measurement conditions in FIG. 4.

FIG. 5 is a diagram that is used to explain the results of the above-mentioned investigation. The vertical axis of FIG. 5 represents the difference $|I_{0.6}-I_{0.3}|$ between a current value $I_{0.6}$ that flows when a voltage in the overcurrent region (0.6 v) is applied and a current value $I_{0.3}$ that flows when a voltage in the limiting current region (0.3 V) is applied. The horizontal axis of FIG. 5 represents the elapsed time after the start of application of the voltage. As shown in FIG. 5, the two current value differences $|I_{0.6}-I_{0.3}|$ showed similar behaviors despite the difference in $SO_2$ concentration. However, when the $SO_2$ concentration was 200 ppm, the current value difference $|I_{0.6}-I_{0.3}|$ was greater at every elapsed time and it took a longer time for the current value difference $|I_{0.6}-I_{0.3}|$ to reach zero compared to the case where the $SO_2$ concentration was 100 ppm.

Figure 6:
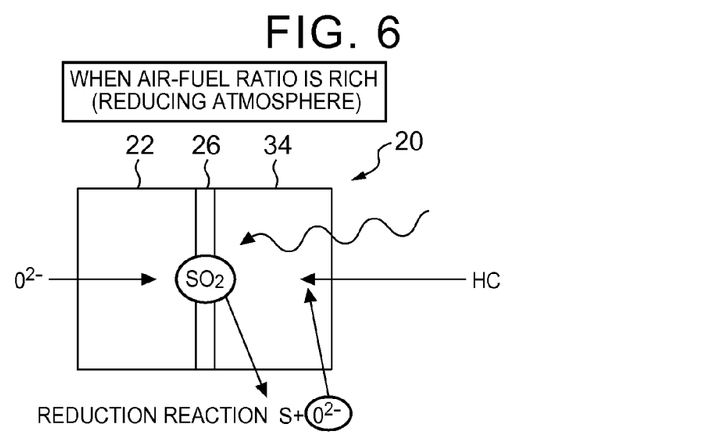
FIG. 6 is a diagram that shows an image of how $SO_2$ is reduced in a rich air-fuel ratio condition.

The results in FIG. 5 indicate that when a voltage in the overcurrent region is applied in a rich air-fuel ratio condition, $SO_2$, which is not supposed to be easily reduced, is reduced and a current flows. FIG. 6 is a diagram that shows an image of how $SO_2$ is reduced in a rich air-fuel ratio condition. The $SO_2$ that is shown in FIG. 6 is derived from exhaust gas. The $SO_2$ has flowed in from the diffusion layer 34 side and has been adsorbed on the surfaces of the electrode 26. Similarly to $SO_2$, the compounds such as HC, CO and $H_2$ (HC is shown in FIG. 5) in the exhaust gas also flow in from the diffusion layer 34 side and reach the surfaces of the electrode 26 in a rich air-fuel ratio condition. It is believed that when a voltage in the overcurrent region is applied between the electrodes at this time, the $SO_2$ on the electrode 26 reacts with HC and gets reduced to S.

In addition, the $SO_2$ concentration around the sensor correlates with the amount of diffusion of $SO_2$ into the diffusion layer 34, and this amount of diffusion of $SO_2$ correlates with the amount of adsorption of $SO_2$ on the electrode surfaces. It is, therefore, believed that it is because the amount of adsorption of $SO_2$ on the electrode surfaces decreased as the reduction of $SO_2$ as described above proceeded and the current value difference $|I_{0.6}-I_{0.3}|$ decreased with the lapse of time in FIG. 5. Similarly, it is believed that it is because the amount of adsorption of $SO_2$ on the electrode surface decreased to zero (or a value close to zero) that the current value difference $|I_{0.6}-I_{0.3}|$ eventually fell to zero.

Figure 7:
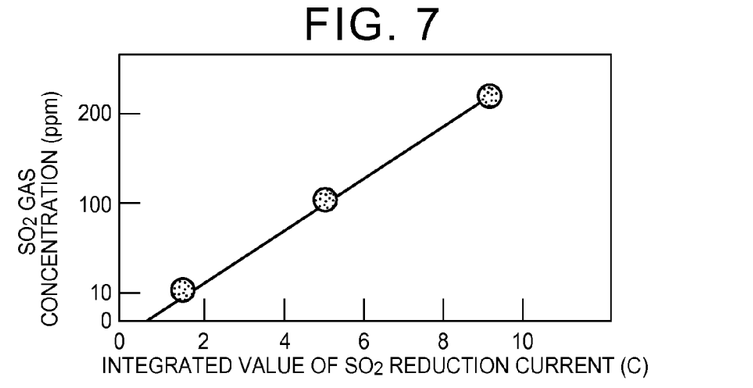
FIG. 7 is a diagram that shows the relationship between the integrated value of the $SO_2$ reduction current and the $SO_2$ concentration around the sensor.

Based on these findings, in this embodiment, the current value difference $|I_{0.6}-I_{0.3}|$ is defined as "$SO_2$ reduction current," and the $SO_2$ concentration around the sensor is detected from an integrated value of the $SO_2$ reduction current. Specifically, the integrated value of the $SO_2$ reduction current corresponds to the area under the characteristic curve that is shown in FIG. 5. FIG. 7 is a diagram that shows the relationship between the integrated value of the $SO_2$ reduction current and the $SO_2$ concentration around the sensor. As shown in FIG. 7, the integrated value of the $SO_2$ reduction current exhibits a generally proportional relationship to the $SO_2$ concentration around the sensor. Thus, the $SO_2$ concentration around the sensor can be detected by obtaining the integrated value of the $SO_2$ reduction current and applying it to the relationship that is shown in FIG. 7. Thus, according to this embodiment, the $SO_2$ concentration around the sensor can be detected using the A/F sensor 14. It should be noted that, in this embodiment, the relationship that is shown in FIG. 7 is stored in advance in the form of a map in the ECU 16.

In this embodiment, S poisoning recovery control is performed for a predetermined period of time if the current value difference $|I_{0.6}-I_{0.3}|$ falls to zero when the integrated value of the $SO_2$ reduction current is obtained. Specifically, the S poisoning recovery control is performed by increasing the temperature of the heating elements 32 to a level higher than that in an ordinary time and forcibly shifting the air-fuel ratio to a rich state. As a result, S that has been generated as a result of the reduction of $SO_2$, residual $SO_2$ that remains unreduced and so on can be desorbed from the electrode 26. This improves the accuracy of the next and subsequent detections of the $SO_2$ concentration.

It is preferred to take the change in the exhaust gas air-fuel ratio into account when the $SO_2$ reduction current is integrated. As mentioned in the description of FIG. 3, the limiting current value increases as the exhaust gas air-fuel ratio is shifted to the leaner side and decreases as the exhaust gas air-fuel ratio is shifted to the richer side. Thus, if the exhaust gas air-fuel ratio changes during the integration of the $SO_2$ reduction current, the current values $I_{0.6}$ and $I_{0.3}$ vary according to the change in the limiting current value. Thus, when the exhaust gas air-fuel ratio changes, it is preferred to correct the current values $I_{0.6}$ and $I_{0.3}$ based on the change in the limiting current value. This improves the accuracy of detection of the $SO_2$ concentration. The change in the limiting current value can be obtained as the difference between the previous and present values of the current value $I_{0.3}$, for example.

[Accessory Components in Electrode 26 and their Amounts of Addition]

Here, accessory components in the electrode 26 and their amounts of addition are described with reference to FIG. 8. As described above, in this embodiment, the amount of adsorption of $SO_2$ on the electrode surfaces is important. Thus, a substance that promotes adsorption of $SO_2$ is preferably added to the electrode 26 to improve the gas sensitivity thereof. Examples of such a substance include alkaline-earth metals (Ca, Sr, Ba and Ra) and rare-earth metals (Y, La, Ce, etc.). Two or more of these metals may be used simultaneously. However, as the amount of adsorption of $SO_2$ on the electrode surface is greater, it is more difficult to regenerate the sensor and it is necessary to perform the above-mentioned S poisoning recovery control for a longer period of time. The present inventors conducted studies in view of this problem, and, consequently, obtained the relationship that is shown in FIG. 8.

Figure 8:
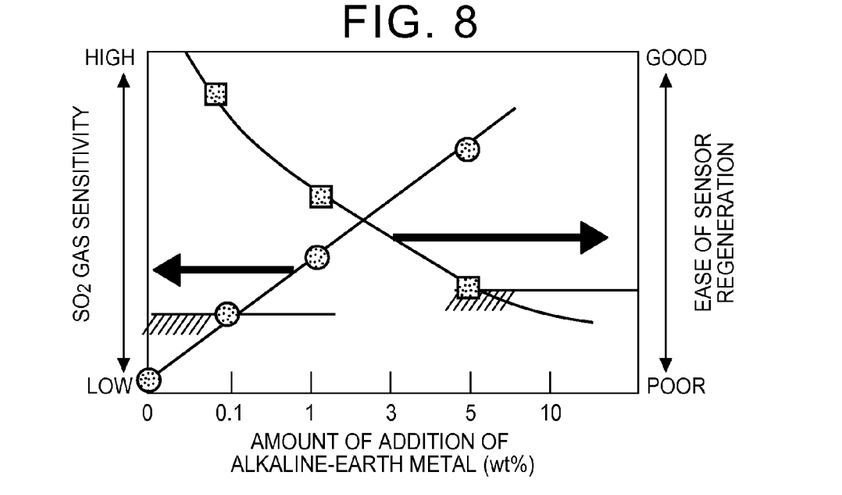
FIG. 8 is a diagram that shows the relationship of the gas sensitivity and the ease of sensor regeneration with the amount of addition of an alkaline-earth metal.

FIG. 8 is a diagram that shows the relationship of the gas sensitivity and the ease of sensor regeneration with the amount of addition of an alkaline-earth metal. As shown in FIG. 8, both the gas sensitivity and the ease of sensor regeneration can be satisfactory when the amount of addition of an alkaline-earth metal is 0.1 to 5.0 wt % based on the whole electrode 26. Thus, the addition of 0.1 to 5.0 wt % of an alkaline-earth metal or rare-earth metal allows the construction of an electrode 26 suitable for the detection of $SO_2$ concentration in this embodiment.

[Specific Processing in this Embodiment]

Figure 9:
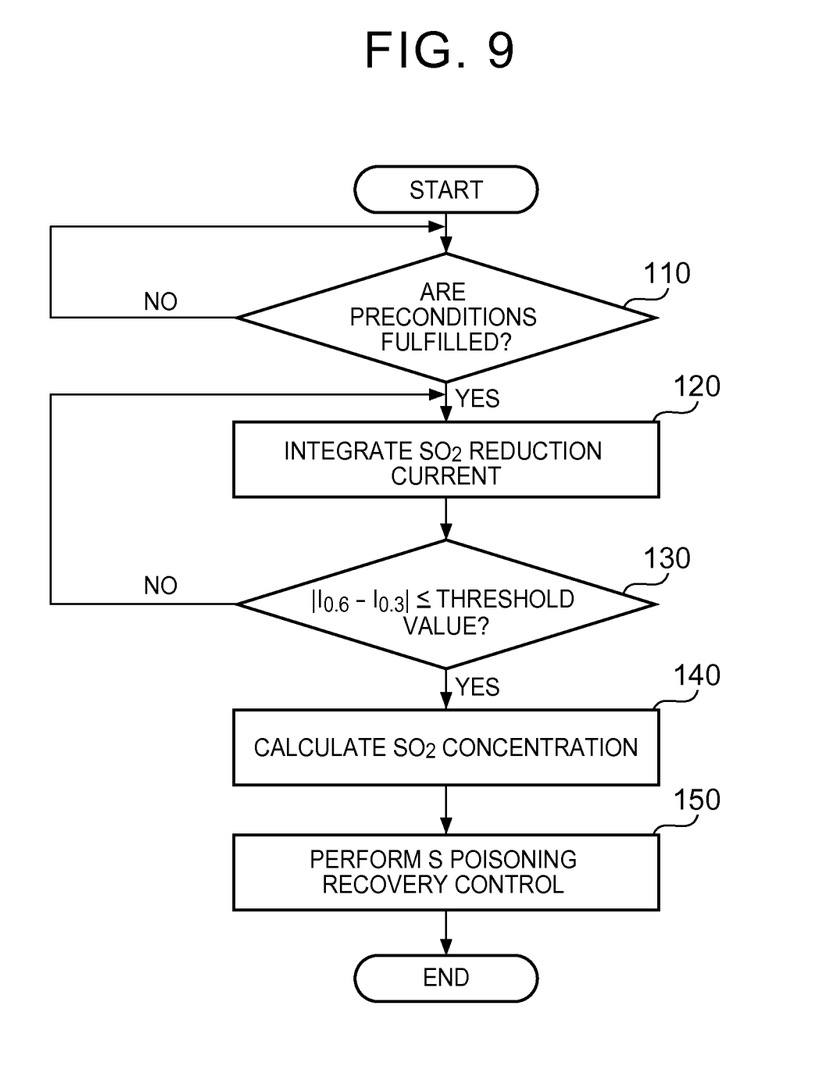
FIG. 9 is a flowchart that shows an $SO_2$ concentration detection routine that is executed by an ECU 16.

Specific processing that realizes the above-mentioned functions is next described with reference to FIG. 9. FIG. 9 is a flowchart that shows an $SO_2$ concentration detection routine that is executed by the ECU 16 in this embodiment. The routine that is shown in FIG. 9 is repeatedly executed on a periodic basis.

In the routine that is shown in FIG. 9, the ECU 16 first determines whether the preconditions are fulfilled (step 110). The preconditions are determined to be fulfilled when (i) the A/F sensor 14 has been activated (warm-up of the sensor has been completed) and (ii) the exhaust gas air-fuel ratio is rich. If it is determined that the preconditions are not fulfilled, the ECU 16 returns to step 110 and determines again whether the preconditions are fulfilled. If it determined that the preconditions are fulfilled, the ECU 16 proceeds to step 120.

In step 120, the ECU 16 integrates the $SO_2$ reduction current. Specifically, the ECU 16 first alternately applies a voltage in the overcurrent region (0.6 v) and a voltage in the limiting current region (0.3 V) between the electrodes 24 and 26, and acquires current signals that are output from the A/F sensor 14. Then, the ECU 16 obtains the current value difference $|I_{0.6}-I_{0.3}|$ from the acquired current signals, and adds a value that is obtained by multiplying the current value difference $|I_{0.6}-I_{0.3}|$ by the voltage application period (the time interval from when 0.6 V is applied to when 0.6 V is applied again, for example) to the previous integrated value.

After step 120, the ECU 16 determines whether the current value difference $|I_{0.6}-I_{0.3}|$ that has been obtained in step 120 fulfills the relationship "current value difference $|I_{0.6}-I_{0.3}| \leq$ threshold value" (step 130). In this embodiment, the threshold value is set to zero. If the relationship "current value difference $|I_{0.6}-I_{0.3}| \leq$ threshold value" is fulfilled, it can be determined that the amount of adsorption of $SO_2$ on the electrode surface has decreased to zero (or a value close to zero). Thus, the ECU 16 proceeds to step 140. If the current value difference $|I_{0.6}-I_{0.3}|>$threshold value, the ECU 16 returns to step 120 and integrates the $SO_2$ reduction current again.

In step 140, the ECU 16 calculates the $SO_2$ concentration. Specifically, the ECU 16 calculates the $SO_2$ concentration around the sensor from the integrated value of the $SO_2$ reduction current that has been obtained in step 120 and the map in FIG. 7.

After step 140, the ECU 16 performs S poisoning recovery control for a predetermined period of time. Specifically, the ECU 16 controls the above-mentioned battery power source to increase the temperature of the heating elements 32 to a level higher than that in an ordinary time. At the same time, the ECU 16 controls the above-mentioned injectors to increase the fuel injection amount in order to make the air-fuel ratio rich.

As described above, according to the routine that is shown in FIG. 9, it is possible to obtain the integrated value of the $SO_2$ reduction current and calculate the $SO_2$ concentration around the sensor. In addition, because S poisoning recovery control is performed for a predetermined period of time when the relationship "current value difference $|I_{0.6}-I_{0.3}|=0$" is fulfilled, it is possible to start desorption of S that has been generated as a result of an $SO_2$ reducing reaction, residual $SO_2$ that remains unreduced and so on from the electrode 26 immediately after the completion of the acquisition of current value data necessary for the detection of $SO_2$ concentration. In other words, the S on the electrode 26 can be desorbed at the best time to improve the accuracy of the next and subsequent detections of the $SO_2$ concentration.

In the above embodiment, the A/F sensor 14, which is installed for the purpose of detecting the exhaust gas air-fuel ratio, can also detect the $SO_2$ concentration. In other words, the A/F sensor 14 is a sensor (dual purpose sensor) that can detect both the $SO_2$ concentration and the exhaust gas air-fuel ratio. However, the A/F sensor 14 may be a sensor (dedicated sensor) that is used to detect only the $SO_2$ concentration. In this case, an A/F sensor that is used to detect the exhaust gas air-fuel ratio is preferably installed in addition to the A/F sensor 14 as a dedicated sensor.

In addition, in the above embodiment, the difference $|I_{0.6}-I_{0.3}|$ between the current value $I_{0.6}$ that flows when 0.6 V is applied between the electrodes 24 and 26 and the current value $I_{0.3}$ that flows when 0.3 V is applied between the electrodes 24 and 26 is defined as "$SO_2$ reduction current." However, it is needless to say that 0.6 V and 0.3 V are values that are shown for illustrative purpose only. In other words, any method that uses the difference between the data of current value that flows when a voltage in the overcurrent region is applied (history of current value) and the data of current value that flows when a voltage in the limiting current region is applied (history of current value) can detect the $SO_2$ concentration in the same manner as described in this embodiment.

In the above embodiment, the A/F sensor 14 corresponds to the "limiting current-type sensor" of the above-mentioned first invention, and 0.3 V and 0.6 V correspond to the "reference voltage" and "SOx detecting voltage," respectively, in the first invention.

In addition, the "SOx concentration detection means" of the above-mentioned first invention is implemented by the ECU 16 executing a sequence of processing that is shown in FIG. 9. In addition, the electrode 26 corresponds to the "detection electrode" of the above-mentioned second invention.

DESCRIPTION OF REFERENCE NUMERALS

10/ engine
12/ exhaust passage
14/ A/F sensor
16/ ECU
20/ sensor element
22/ solid electrolyte
24, 26/ electrode
28/ air duct
30/ heater base material
32/ heating element
34/ diffusion layer

The invention claimed is:

1. An SOx concentration detection device comprising:
an electronic control unit electrically connected, on an input side, to a plurality of engine control sensors and electrically connected, on an output side, to a plurality of actuators, the electronic control unit for executing predetermined programs based on input information from the plurality of engine control sensors; and
a limiting current-type sensor including a solid electrolyte and a pair of electrodes, the solid electrolyte having oxide ion conductivity, and the pair of electrodes being provided on opposite sides of the solid electrolyte,
the limiting current-type sensor configured to generate a limiting current corresponding to a concentration of a specific component in exhaust gas from an internal combustion engine when a predetermined voltage is applied between the pair of electrodes;
the electronic control unit programmed to:
apply a reference voltage and an SOx detecting voltage between the pair of electrode when an exhaust gas air-fuel ratio of the internal combustion engine is on rich side of stoichiometry, the reference voltage being a voltage in a limiting current region that includes the predetermined voltage, and the SOx detecting voltage being a voltage in a voltage region higher than the limiting current region,
acquire an SOx detecting output that is output from the limiting current-type sensor when the SOx detecting voltage is applied, and acquire a reference output that is output from the limiting current-type sensor when the reference voltage is applied, and
detect a SOx concentration in the exhaust gas from the internal combustion engine using histories of the SOx detecting output and the reference output that are generated before an output difference between the SOx detecting output and the reference output falls to or below a set value.

2. The SOx concentration detection device according to claim 1,
wherein the pair of electrodes include a detection electrode,
the detection electrode is provided on an exhaust gas contacting surface of the solid electrolyte, and
the detection electrode contains 0.1 to 5.0 wt % of at least one metal that is selected from a group that consists of alkaline-earth metals and rare-earth metals.

3. The SOx concentration detection device according to claim 1,
wherein the electronic control unit is further programmed to control the exhaust gas air-fuel ratio to the richer side of stoichiometry and heat the sensor to a predetermined temperature at which sulfur components that have been adsorbed on the pair of electrodes can be desorbed when the output difference falls to or below the set value.

* * * * *

UNITED STATES PATENT AND TRADEMARK OFFICE
CERTIFICATE OF CORRECTION

Page 1 of 1

PATENT NO.         : 9,753,005 B2
APPLICATION NO.    : 14/760528
DATED              : September 5, 2017
INVENTOR(S)        : Tetsuya Kato et al.

It is certified that error appears in the above-identified patent and that said Letters Patent is hereby corrected as shown below:

On the Title Page

And in the Specification, at Column 1, Line 1, change the title from:
"SOX CONCENTRATION"
To:
"SOx CONCENTRATION"

Signed and Sealed this
Twenty-fourth Day of July, 2018

Andrei Iancu
*Director of the United States Patent and Trademark Office*